US010321975B2

(12) United States Patent
Burns et al.

(10) Patent No.: US 10,321,975 B2
(45) Date of Patent: Jun. 18, 2019

(54) ROOT CANAL DEBRIDEMENT EFFECTIVENESS DEVICE AND METHOD

(71) Applicant: Ormco Corporation, Orange, CA (US)

(72) Inventors: Steven Joseph Burns, Marina del Rey, CA (US); Emanuele Maretto, Orange, CA (US); Abhigyan Som, Brea, CA (US); Carlos Alberto Munoz, Orange, CA (US); Matteo Bosisio, Lugano (CH); Gopikrishnan Soundararajan, Santa Clara, CA (US); Tuyen Nguyen, Buena Park, CA (US); M. Reza Mehrabi, Tujunga, CA (US)

(73) Assignee: Ormco Corporation, Orange, CA (US)

( * ) Notice: Subject to any disclaimer, the term of this patent is extended or adjusted under 35 U.S.C. 154(b) by 10 days.

(21) Appl. No.: 15/605,094

(22) Filed: May 25, 2017

(65) Prior Publication Data

US 2017/0340413 A1 Nov. 30, 2017

Related U.S. Application Data

(60) Provisional application No. 62/341,822, filed on May 26, 2016.

(51) Int. Cl.
*A61C 5/50* (2017.01)
*A61C 5/40* (2017.01)
(Continued)

(52) U.S. Cl.
CPC .............. *A61C 5/50* (2017.02); *A61C 1/0015* (2013.01); *A61C 1/0092* (2013.01); *A61C 1/088* (2013.01);
(Continued)

(58) Field of Classification Search
CPC .......... A61C 5/40; A61C 5/50; A61C 17/0208
See application file for complete search history.

(56) References Cited

U.S. PATENT DOCUMENTS

| 4,947,245 A | * | 8/1990 | Ogawa ............... A61B 1/00101 348/66 |
| 6,997,245 B2 | * | 2/2006 | Lindemuth ............. B22F 7/004 165/104.21 |
| 2013/0040267 A1 | * | 2/2013 | Bergheim ................ A61C 3/03 433/216 |

FOREIGN PATENT DOCUMENTS

| EP | 0830851 A1 | 3/1998 |
| EP | 2682136 A1 | 1/2014 |

(Continued)

OTHER PUBLICATIONS

International Searching Authority, Search Report and Written Opinion issued in corresponding International Application No. PCT/US2017/034428 dated Sep. 5, 2017 (21 pages).

*Primary Examiner* — Ralph A Lewis
(74) *Attorney, Agent, or Firm* — Wood Herron & Evans LLP

(57) ABSTRACT

A method for continuously evaluating the effectiveness of debridement of a root canal of a tooth, the tooth having an open access cavity and an apex end, includes delivering a fluid to the open access cavity of the tooth, evacuating the fluid near the apex end of the tooth such that the fluid flushes most of the root canal before being evacuated, and continuously evaluating the evacuated fluid for at least one of a presence of debris, a concentration level of the debris, or a type of the debris. An apparatus for use in debriding a root canal of a tooth includes a microcannula or a macrocannula configured to evacuate a fluid in the root canal, and a sensing mechanism fluidically coupled to the microcannula or the (Continued)

macrocannula, the sensing mechanism configured to continuously sense debris in the evacuated fluid in real time.

37 Claims, 10 Drawing Sheets

(51) Int. Cl.
    *A61C 1/00*     (2006.01)
    *A61C 1/08*     (2006.01)
    *A61C 17/02*     (2006.01)
    *A61C 19/04*     (2006.01)
    *A61C 19/06*     (2006.01)
    *A61K 6/00*     (2006.01)
    *G01N 21/53*     (2006.01)
    *G01N 21/64*     (2006.01)

(52) U.S. Cl.
    CPC ............ *A61C 5/40* (2017.02); *A61C 17/0208* (2013.01); *A61C 19/04* (2013.01); *A61C 19/063* (2013.01); *A61K 6/0035* (2013.01); *G01N 21/532* (2013.01); *G01N 21/6428* (2013.01); *G01N 2021/6439* (2013.01); *G01N 2201/06113* (2013.01)

(56) References Cited

FOREIGN PATENT DOCUMENTS

| | | |
|---|---|---|
| JP | 2004-313659 A | 11/2004 |
| KR | 20120047227 A | 5/2012 |

\* cited by examiner

ROOT CANAL DEBRIDEMENT EFFECTIVENESS DEVICE AND METHOD

FIELD OF THE INVENTION

This invention relates to a device and method for sensing the effectiveness of root canal debridement.

BACKGROUND OF THE INVENTION

A root canal treatment may be used to preserve a tooth that has or could develop a diseased pulp cavity. To prevent bacterial proliferation within the root or pulp canal of the tooth, the canal is enlarged without excessively weakening the root's wall in order to: 1) mechanically remove as much of the root canal contents as is possible and 2) allow the introduction of irrigants into the root canal space that dissolve and disinfect organic debris, thus minimizing the presence of bacteria, as well as clearing the walls of the root canal of calcific debris created during instrumentation. After completing steps 1 and 2, the root canal is typically filled or obturated with a material such as gutta-percha and a sealer to occlude the pulp cavity and thus seal the root canal.

Irrigation assists in removing debris and necrotic material remaining after the endodontic files, bores, and reamers used during the removing and shaping steps of the procedure. Although the irrigant preferably is capable of dissolving or disrupting soft tissue remnants to permit their removal, the irrigant may be any suitable liquid such as water or various alcohols. More particularly, although some degree of debridement is preferred, any fluid may be used to flush debris from the root canal. General examples of appropriate irrigants include hydrogen peroxide and sodium hypochlorite.

In essence, the procedure goal is to convert the root into a devitalized tissue autograft. As such, it is important that the root canal is properly cleared of all debris before being filled. However, it is nearly impossible to visually determine if a root canal on a tooth, or analogous tiny channels, have been fully cleaned and flushed. Further, due to the small diameter of the canal (e.g., about 0.25 mm) and the curved geometry, it cannot be easily imaged using current technology. In addition, roots have complex morphology including accessory canals. As a result, current techniques involve relying on the experience and skills of the practitioner cleaning the canals to help assure a clean canal for an effective procedure. Failing to remove all of the necrotic tissue and bacteria often causes the procedure to fail, at which point the patient must have the procedure redone or have the tooth extracted. Thus, providing an improved method of determining whether the root canal is clean before obturation will improve the efficacy of the root canal treatment.

SUMMARY OF THE INVENTION

The present invention provides a method for continuously evaluating the effectiveness of debridement of a root canal of a tooth, the tooth having an open access cavity and an apex end. The method includes delivering a fluid to the open access cavity of the tooth, evacuating the fluid near the apex end of the tooth such that the fluid flushes most of the root canal before being evacuated, and continuously evaluating the evacuated fluid for at least one of a presence of debris, a concentration level of the debris, or a type of the debris.

The present invention provides an apparatus for use in debriding a root canal of a tooth includes a microcannula or a macrocannula configured to evacuate a fluid in the root canal, and a sensing mechanism fluidically coupled to the microcannula or the macrocannula, the sensing mechanism configured to continuously sense debris in the evacuated fluid in real time.

The present invention provides a method for evaluating the effectiveness of debridement of a root canal of a tooth, the tooth having an open access cavity and an apex end. The method includes delivering a fluid to the open access cavity of the tooth, evacuating the fluid near the apex end of the tooth such that the fluid flushes the root canal before being evacuated, and evaluating the evacuated fluid for at least one of a presence of debris, a concentration level of the debris, or a type of the debris using a sensing mechanism. The sensing mechanism has a configuration that is continuous, semi-batch, or batch.

The present invention provides an apparatus for use in debriding a root canal of a tooth. The apparatus includes a delivery tube for delivering fluid to the root canal and a sensing mechanism configured to continuously sense debris in the fluid. The sensing mechanism includes a first electrode, a second electrode comprising a microcannula or a macrocannula configured to evacuate the fluid in the root canal, and a sensor coupled to the first and second electrodes.

The present invention provides a method for debriding a root canal of a tooth, the tooth having an open access cavity and an apex end. The method includes delivering a fluid to the open access cavity of the tooth, the fluid including an aqueous solution. The aqueous solution comprises an amount of $CaNa_2EDTA$ and 2.5% stabilized sodium hypochlorite.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
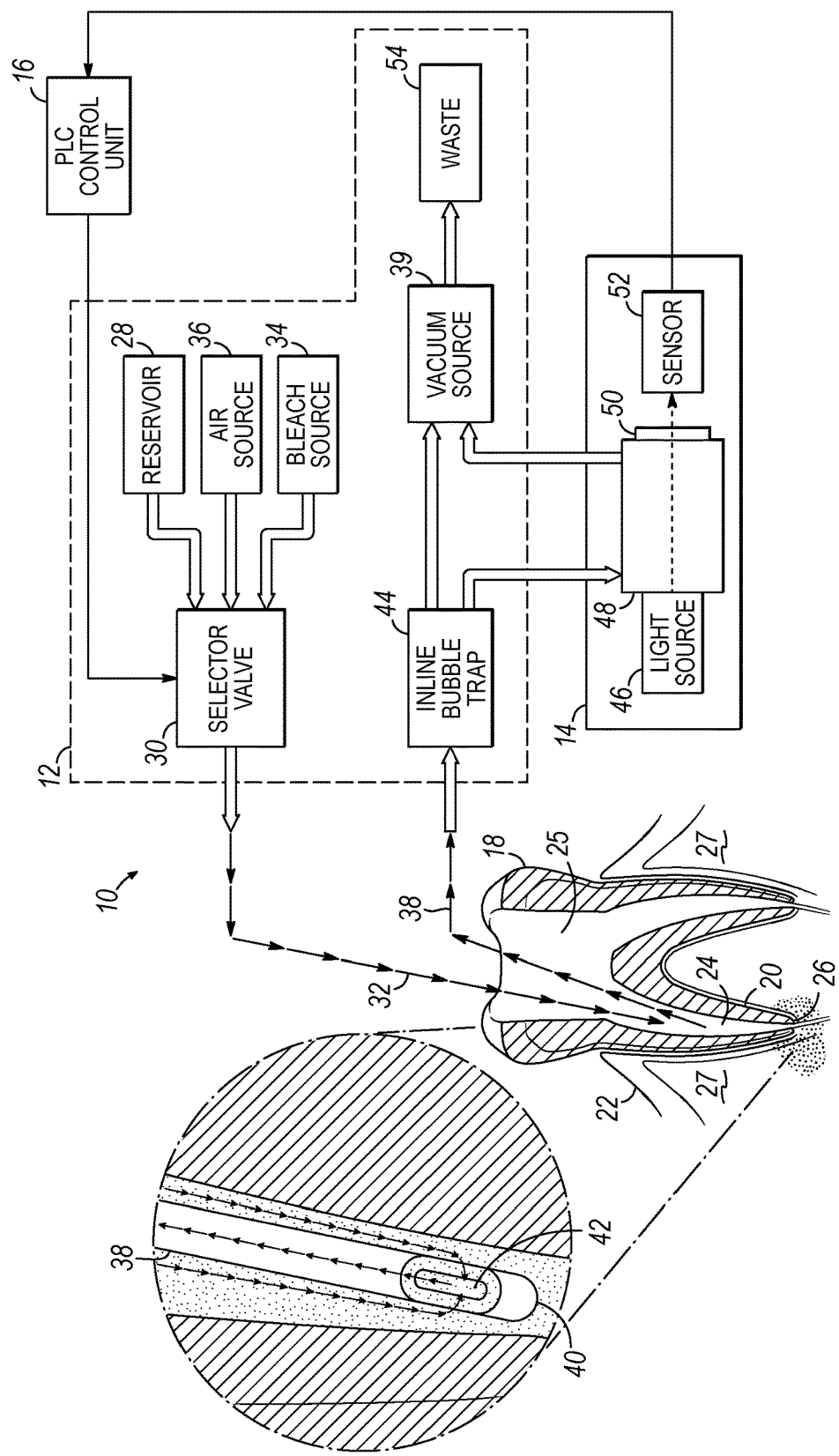
FIG. 1 is a schematic of a system for determining the effectiveness of root canal debridement according to an embodiment.

Referring first to FIG. 1, in an embodiment of the invention, a system 10 for determining the effectiveness of root canal debridement or the presence of bacteria in fluids evacuated from a root canal includes a canal evacuation system 12, a sensing mechanism, shown as a spectrometer 14, and a controller 16. The system 10 is used during a root canal treatment of a tooth 18 after the root 20 has been shaped. The root 20 extends through the gums 22. In approximately the middle of the root 20 extending almost the entire length of the root 20 is the root canal 24, which extends from one end near the crown portion of the tooth 18 to an apex 26 at the tip of the root 20. As shown in FIG. 1, the non-visible portion of the tooth 18 extending past the gums 22 is surrounded by periapical tissue 27. Stripping the root 20 results in a large quantity, both in terms of size and amount, of debris within the root canal 24. The canal evacuation system 12 is used to cleanse the stripped root canal 24 by delivering an irrigant to an open access cavity 25 of the tooth 18. The irrigant, which mixes with the debris, is then evacuated from the root canal 24 by the canal evacuation system 12, which applies a negative pressure within the root canal 24. The debris in the evacuated irrigant may include viable tissue (e.g., dental pulp, dentin, and blood), cells, necrotic tissue, and bacteria, among other things. The evacuated material is then directed to the spectrometer 14 to evaluate the absorbance (e.g., UV wavelength, visible wavelength, infrared wavelength) of the evacuated material. The controller 16 then analyzes the data from the spectrometer 14 to determine if debris is present in the evacuated material. Depending on the results, the controller 16 may determine the flushing of the root canal 24 should continue or that the root canal 24 is sufficiently cleansed. The system 10 is described in further detail below.

Figure 2:
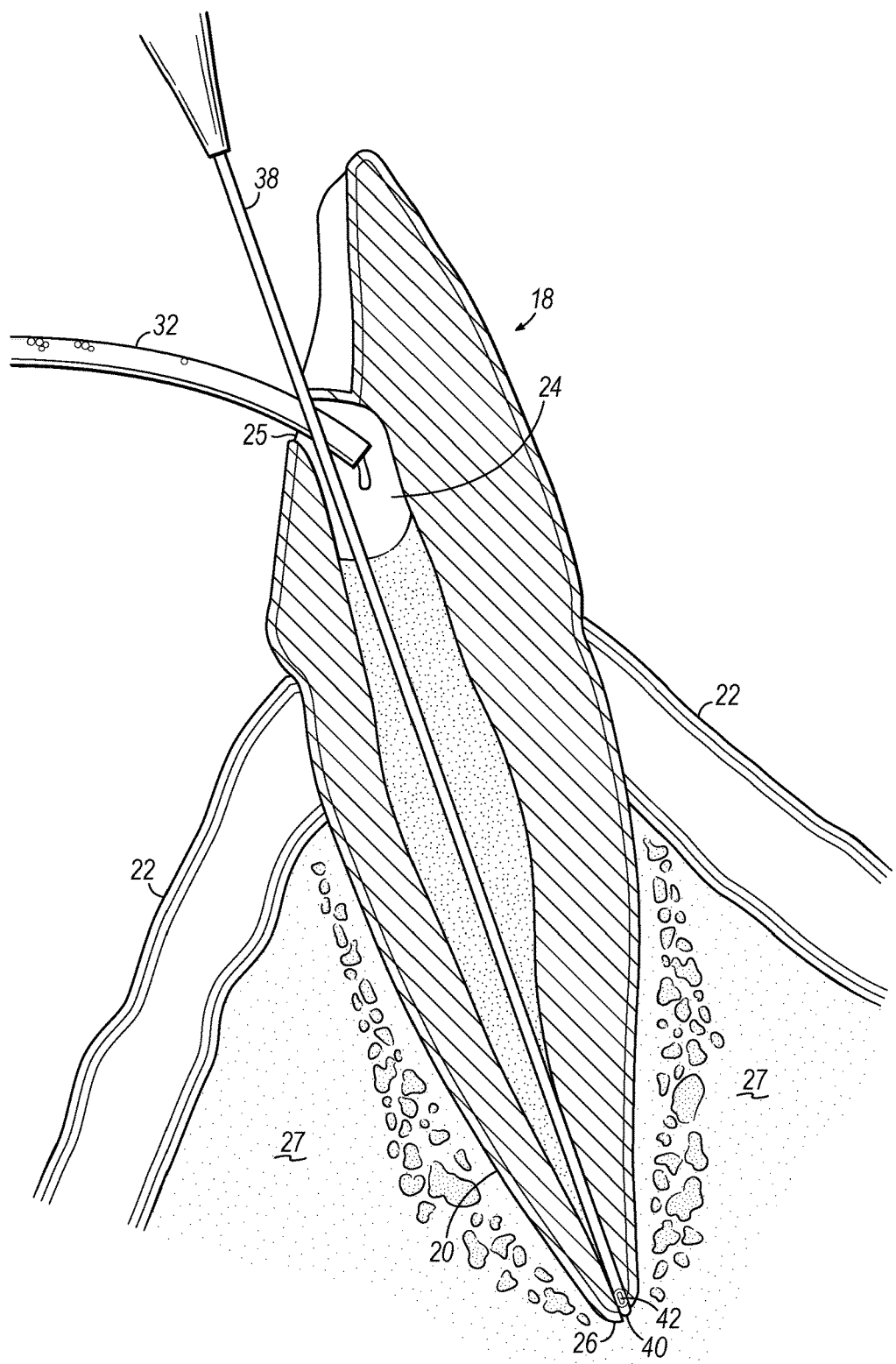
FIG. 2 is a cut away side view of a tooth showing a prior art canal evacuation system suitable for use in the system of FIG. 1.

With reference now to FIGS. 1 and 2, in an embodiment, the canal evacuation system 12 includes a reservoir 28, a selector valve 30, and a delivery tube 32. The reservoir 28 may include, for example, a concentrated detergent suitable for use in debriding a root canal. The selector valve 30 is coupled to the reservoir 28, a bleach source 34, and optionally an air source 36. The bleach may be used to clean the root canal 24, and the air may be used to clear out the root canal 24 before a reading is taken by the sensing mechanism (described further below). One of ordinary skill will recognize that a number of bio-compatible irrigants may be used to flush the root canal 24 and determine whether debris is present. For example, the irrigant may be water, saline, phosphate-buffered saline, sodium hypochlorite (NaClO), ethylenediaminetetraacetic acid (EDTA), modified EDTA, or a mixture of concentrated detergent and water. The irrigant is delivered to the root canal 24 via the delivery tube 32. In an embodiment, a second reservoir (not shown) contains a second irrigant. For example, the reservoir 28 may contain EDTA, and the second reservoir may contain NaClO. A first flush of EDTA may be used to remove inorganic matter, and a second flush of NaClO may be used to remove the remaining organic matter.

The canal evacuation system 12 further includes a microcannula 38 and a vacuum source 39. While the system 12 is shown as including the microcannula 38, a system according to another embodiment may include a macrocannula. As described in U.S. Pat. No. 8,827,705, which is incorporated by reference herein in its entirety, the microcannula 38 is typically made of a metallic material such as stainless steel or titanium and, in an embodiment therein, has an outside diameter of 0.014 inches. The microcannula 38 has a tip 40 that is welded shut and rounded and includes a side vent 42. In an embodiment therein, the side vent 42 is approximately 0.75 mm long beginning at a point approximately 0.5 mm from the end of the tip 40. Further, the microcannula 38 may be sized so as to be able to fit into the root canal 24 so that it extends towards the apex 26 with the side vent 42 extending as close to the end of the root canal 24 as possible but without extending into the periapical tissue 27. A vacuum is applied to the microcannula 38 during or after delivery of the irrigant. In this manner, the irrigant is drawn down through the root canal 24 into the apical portion, that is, the bottom approximately 4-5 mm portion of the root canal 24 ending at the apex 26. Since the tip 40 is closed, the irrigant is drawn into the side vent 42. In this manner, the irrigant does not extend past the tip 40 and cannot be drawn into the periapical tissue 27 due to the vacuum which exists at the side vent 42. By this technique, the irrigant creates shear forces along the walls of the root canal 24 to dislodge debris on the wall and to clean and disinfect the root canal 24. Further, the irrigant flushes the apical portion of the root canal 24, removing any remnants of debris and does not allow the irrigant to enter the periapical tissue 27. In other embodiments, throughout the procedure, the irrigant may be delivered to the open access cavity 25 at the coronal side or at a different depth of the root canal 24. Further, the fluid may be evacuated near the apex 26 or at different depth in the root canal 24.

With reference again to FIG. 1, the microcannula 38 is fluidically coupled to the spectrometer 14. In an embodiment, the spectrometer 14 is a mini UV long pathlength spectrometer. The evacuated material is delivered from the root canal 24 to the spectrometer 14 to determine whether debris is still being flushed from the root canal 24. Bubbles generated from the turbulence of the irrigant flowing through the root canal 24 generate signal noise. To account for this, in an embodiment, the evacuated material may flow through a bubble trap 44 to eliminate the bubbles, which should substantially stabilize the signal. The bubble trap 44 may be a vacuum assist bubble trap or a non-vacuum assist bubble trap. Further, depending on the configuration of the spectrometer 14, a sample of the evacuated material may optionally be directed to the spectrometer 14 with the remainder being treated as waste. As the evacuated material passes through the sensing mechanism, the spectrometer 14 evaluates the UV absorbance of the evacuated material. More specifically, the spectrometer 14 includes a light source 46, a liquid waveguide capillary cell or a long pathlength capillary cuvette 48, a diffraction grating 50, and a sensor 52. As the evacuated material flows through the long pathlength capillary cuvette 48, the light source 46 emits UV light, which is separated into the different wavelengths of light by the diffraction grating 50. The sensor 52 measures the characteristics of the light that passes through the evacuated material. The pathlength of the capillary cuvette 48 may be from about 50 mm to about 100 mm, and this relatively long pathlength results in increased sensitivity to permit reading the low concentration levels of the debris in the evacuated material. The diameter of the capillary cuvette 48 may be, for example, from about 50 micron to about 4 mm, about 50 micron to about 1 mm or from about 200 to about 400 micron. The capillary cuvette 48 may be coated to reduce stray light from interfering with the sensing mechanism. After the evacuated material has flown through the spectrometer 14, the evacuated material is sent to a waste receptacle 54. Before or after use, the system 10 may be configured to flush the system with the irrigant in which the irrigant bypasses the sensing mechanism.

With reference again to FIG. 1, the controller 16 is coupled to the sensing mechanism and is configured to determine if debris is present in the evacuated material based on data received from the sensor 52. In one embodiment, the sensor 52 outputs a signal to the controller 16 such as a voltage, a digital absorbance value, or a digital transmittance value. During the cleaning of the root canal 24, the signal will drop as the amount of debris in the evacuated material decreases. The controller 16 measures the change in signal output. The change in the signal is an indication of the progress of the cleaning and disinfecting of the root canal 24. Because the irrigant is evacuated from near the apex 26, the signal relates to the cleanliness of the entire root canal 24 as opposed to a signal from a sample taken from one location in the root canal 24. Further, because the sampling is continuous and in real time, the clinician is not required to interrupt the cleaning process to take a measurement. Additionally, the risk of sample contamination is mitigated compared to taking a sample manually. While the evaluation may include continuous real time monitoring, the evaluation may alternatively include a discrete (high/low) sampling rate.

When the signal baselines, the controller 16 may be configured to alert the clinician. In an embodiment, the signal given by the irrigant without any debris present may be programmed into the controller 16 or set as a tare or used in a "zeroing" function. In various embodiments, the signal may baseline at or near the tare signal or the rate of change of the signal may be monitored and the signal may baseline when the rate of change decreases. The alert could be, for example, an audible tone. In an embodiment, the audible tone may be continuously emitted or emitted on command. Further, in an embodiment, the controller 16 is configured to differentiate between various types of debris. For example, the controller 16 may be configured to differentiate between different signals sent by the sensor 52 indicating the presence of tissue content or blood content in the irrigant. In such an embodiment, the controller 16 may include a duo-tone feature, which could tonally differentiate between, for example, tissue content and blood content in the evacuated material. For example, a sinewave tone could indicate by pitch the level of blood debris, while a sawtooth wave could indicate by pitch the level of protein debris. Together, these tones would be disharmonious indicating a dirty root canal 24 and harmonic for a clean root canal 24. One of ordinary skill will recognize that the controller 16 may be configured to alert the clinician to the presence, concentration level, size, and/or type of debris using a variety of techniques.

Figure 3A:
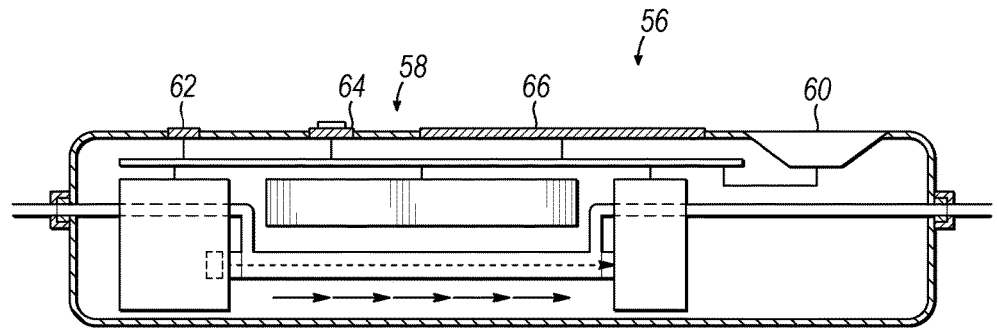
FIG. 3A is a cross-sectional view of an in-line handle including the sensing mechanism of FIG. 1.
Figure 3B:
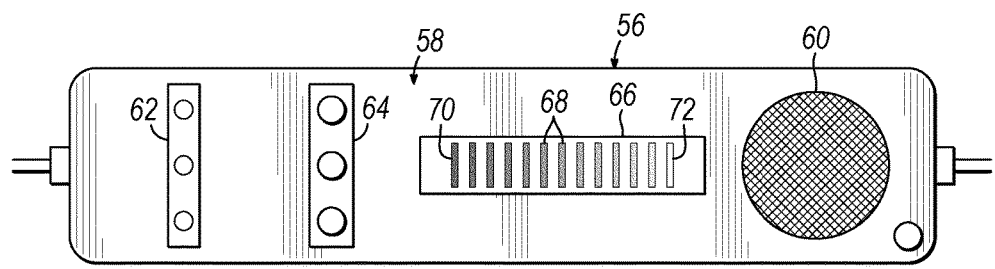
FIG. 3B is a top view of the in-line handle of FIG. 3A.

With reference to FIGS. 3A and 3B, in an embodiment, the system 10 includes an in-line handle 56 containing the spectrometer 14, the controller 16, and a visual graphic user interface ("GUI") 58. The handle 56 may also include a speaker 60 for emitting an auditory tone. The controller 16 is configured to display the presence and/or concentration level of debris in the evacuated material using the GUI 58. The GUI 58 may also be used to visually differentiate between sizes and types of debris (not shown). The GUI 58 may include a variety of visual indicators. In an embodiment, the GUI 58 includes a status indicator 62, function buttons 64, and a cleanliness indicator 66. The status indicator 62 displays whether the system 10 is powered on, ready to analyze a sample from the evacuated material, or currently analyzing a sample. The function buttons 64 may be used to initiate a variety of functions on the handle 56, such as to "zero" the signal. The cleanliness indicator 66 alerts the clinician to the relative cleanliness of the evacuated sample. In an embodiment, the cleanliness indicator 66 includes a row of indicator bars 68. A first indicator bar 70 indicates a dirty sample, and a last indicator bar 72 indicates a clean sample. The indicator bars 68 may range in color from, for example, red at the first indicator bar 70 to green at the last indicator bar 72. The controller 16 may be configured to light up the appropriate indicator bar 68 based on the signal received from the sensor 52. While the GUI 58 is illustrated as a part of the in-line handle 56, the GUI 58 may be located elsewhere. In various embodiments (not shown), the GUI 58 may be located in a docking station for the system 10, computer in the dental suite, or an electronic device such as Google Glass or Microsoft Hololens.

A method of evaluating the effectiveness of debridement of the root canal 24 is now described with reference to FIGS. 1-3B. In an embodiment, the reservoir 28 contains a flush solution of EDTA, which is used to debride root canals. The clinician may optionally clear out the root canal 24 with air from the air source 36 before delivering the EDTA solution and taking a reading with the spectrometer 14. To flush the root canal 24, the EDTA solution is delivered to the root canal 24 via the delivery tube 32. The vacuum source 39 is activated to draw the irrigant through the root canal 24 and out of the microcannula 38. The evacuated irrigant may then pass through the bubble trap 44 to reduce or eliminate any bubbles. Depending on the configuration of the sensing mechanism, the evacuated material may optionally be divided where a sample is sent through the handle 56 and the remainder is sent to the waste receptacle 54. As the sample enters the handle 56, it passes through the long pathlength capillary cuvette 48 of the spectrometer 14. Light from the light source 46 is directed through the sample and is sensed by the sensor 52. The debris in the sample may absorb the UV light at distinct wavelengths. For example, proteins may heavily absorb at 280 nm, oxyhemoglobin may heavily absorb at 420 nm or 540 nm, and an iron-EDTA chromophore complex may absorb at 254 nm or 290 nm. Root canal tissue may be sensed with good resolution at a wavelength in a range from 296 nm to 320 nm, as described in further detail in Example 1. Thus, the controller 16 may evaluate the signal from the sensor 52 to determine if debris is present in the evacuated material. The sensor 52 delivers a signal to the controller 16. The controller 16 may cause the speaker 60 to emit an auditory tone or the GUI 58 to indicate the cleanliness of the sample. Depending on the results, the controller 16 may determine the flushing of the root canal 24 should continue because the root canal 24 is not sufficiently cleansed or that flushing may cease because the root canal 24 is sufficiently cleansed. When the controller 16 indicates that the sample is sufficiently clean, the clinician may stop the delivery of the irrigant to the root canal 24.

Referring again to FIG. 1, in an embodiment of the invention, the canal evacuation system 12 is configured to deliver a reagent to the root canal 24, which will react in the presence of debris. More particularly, the reservoir 28 may include, for example, a protein reagent. The circulation of the reagent in the root canal 24 is ideal to expose the reagent to pulp, blood, and marrow remnants that cause a change in a detectable property in the reagent, such as a color change. The reagent is evacuated by the canal evacuation system 12 and directed to the spectrometer 14 to evaluate the color absorbance of the reagent. As described above, the controller 16 then analyzes the data received by the spectrometer 14 to determine if debris is present in the root canal 24.

Because the level of debris in the root canal 24 may be on the level of micrograms, a purpose of the reagent is to chemically magnify the signal caused by debris in the root canal 24. One of ordinary skill will recognize that a number of bio-compatible reagents may be used to evaluate the cleanliness of the root canal 24. For example, the reagent may be Folin Ciolcateau reagent, bicinconic acid reagent, or Bradford reagent (Coomassie stain). The reagent may also be Folin Ciolcateau or bicinconic acid reagent with a non-ionic surfactant. In one embodiment, the reagent may include a bicinchonic acid/cuprous (++) sulfate system, which will not stain dentition.

Further, in an embodiment, the reagent may be a luminescence mediated indicator, such as a fluorescent dye. As described in U.S. Patent Application Publication No. US2012/0034579A1, which is incorporated by reference herein in its entirety, such an indicator is capable of exhibiting a detectable and/or measurable change in the presence of a cell or cell population. As described therein, the measurable or detectable change may be the quenching or activation of a certain luminescent behavior (e.g. luminescence, intensity of luminescence above a predetermined threshold or a certain distinct wavelength of luminescence). The change may indicate a variety of results including, for example: presence or absence of viable cells, presence or absence at predetermined threshold of viable cells, risk factor of presence of viable cells, population or concentration of viable cell population, or presence and type of viable cells. As further described therein, a fluorescence mediated indicator is biocompatible and, preferably, is a vital dye (i.e., the indicator itself does not cause cell death). Thus, in accordance with the present embodiment, when the indicator is delivered to the root canal 24 via the delivery tube 32, the indicator begins interacting with any debris that may be present. The clinician or the controller 16 may then activate the vacuum source 39 to draw the reagent through the root canal 24 and out of the microcannula 38. As the evacuated sample moves through the sensing mechanism, the sensing mechanism examines the evacuated sample for the expected detectable and/or measurable change of the indicator. The controller 16 may then alert the clinician to indicate whether the indicator changed due to the presence of debris in the root canal 24.

A person of ordinary skill will recognize that a number of bio-compatible indicators may be used to evaluate the cleanliness of the root canal 24. Exemplary indicators include: 4',6-diamidino-2-phenylindole (DAPI), enhanced blue fluorescent protein (EBFP), Hoechst 33258 dye, 7-hydroxy-4-methylcoumarin, quinine sulfate, 4-methylumbelliferone, 5-carboxyfluorescein (5-FAM), Calcein, DiO, fluorescein, FLUO-3, FLUO-4, enhanced green fluorescent protein (EGFP), green fluorescent protein (GFP), Oregon Green 514, Rhodamine Green, SYBR Gold, SYBR Green, SYTO 9, SYTOX Green, yellow fluorescent protein (YFP), LIVE/DEAD BacLight, Alexa Fluor 555, Cy3, ethidium bromide, ethidium homodimer-1, propidium iodide, Resorufin, red fluorescent protein (RFP), Rhod-2, Rhodamine Red, SYTOX Orange, carboxytetramethylrhodamine (TAMRA), Texas Red, tetramethylrhodamine (TRITC), Allophycocyanin, Cy5, DRAQ5, SYTOX Red, Indocyanine green, sodium fluorescein, carboxyfluorescein, methylene blue, or ProSense 750. Exemplary indicators also include pegylated pyrenes, such as pyrene-PED-biotin and mPEG-Pyrene having a molecular weight of about 1,000-30,000 Da.

The method of evaluating the effectiveness of debridement of the root canal 24 as described above with reference to FIGS. 1-3B applies equally to the use of a reagent. In various embodiments, the reagent may be delivered continuously or in a pulsatile manner. Compared to a continuous delivery of the reagent, a pulsatile feature reduces the amount of reagent required, which reduces the cost of the procedure and reduces risk of exposing patient to a possibly bad taste of the reagent. During the cleaning of the root canal 24, the amount of debris in the evacuated material decreases, which causes less of a change in the reagent (e.g., color, luminescence, fluorescence, etc.) and results in a signal drop. When the signal baselines, the controller 16 may be configured to alert the clinician that the evacuated material is sufficiently free of debris.

While the sensing mechanism shown in FIG. 1 is a UV spectrometer, it should be recognized that the configuration of the sensing mechanism, as well as the measured attribute, may vary based on the application. In an embodiment, the light source 46 may be a RGB LED, and the sensor 52 may be a photo detector, such as a photodiode. Additionally, the light source 46 and the sensor 52 may be integrated in one component. In an embodiment, a transmissive sensor includes the light source 46, which may be an infrared (IR) emitter, and the sensor 52, which may be a photo detector, in which the evacuated material flows through an aperture between the light source 46 and the sensor 52. As debris passes through the optical beam, the light energy reaching the sensor 52 decreases, which indicates that debris is present. In another embodiment, the turbidity (i.e., the light scattering) of the evacuated material is measured by the sensor 52. The turbidity signal may be increased by adding a volume exclusion compound, such as liposomes or a long molecular weight polyethylene glycol (e.g., PEG-1000 to 8000). In an embodiment, the irrigant is an aqueous solution including 15% PEG-8000 and 17% $Na_2EDTA$ (disodium salt of EDTA), which results in an increased strength of the turbidity signal compared to an EDTA solution. In other various embodiments, the sensing mechanism may include cell trapping, such as mechanical traps, ultrasonic wave traps, electrical traps, antibodies capture, and optical traps.

In an embodiment, a sensing mechanism including optics elements and electronics may have dimensions of 50 mm×50 mm×30 mm or less. A lock-in detection method may be used to reduce the electrical noise of unwanted ambient light. Further, the sensing mechanism may include a secondary photodiode, which may, for example, be used to monitor the light source power for an intensity measurement or as a reference for the lifetime measurement. This configuration may, for example, detect a scattered light intensity from or a fluorescence marker in a 200 to 10 μm (or smaller) particle in microfluidic channels coupled to the sensor (e.g., 1 mm channel or preferably 500 μm or less at a 500 Hz sampling frequency). In an embodiment, the sensing mechanism may allow the spectral filters to be exchanged according to the intended application.

Figure 4:
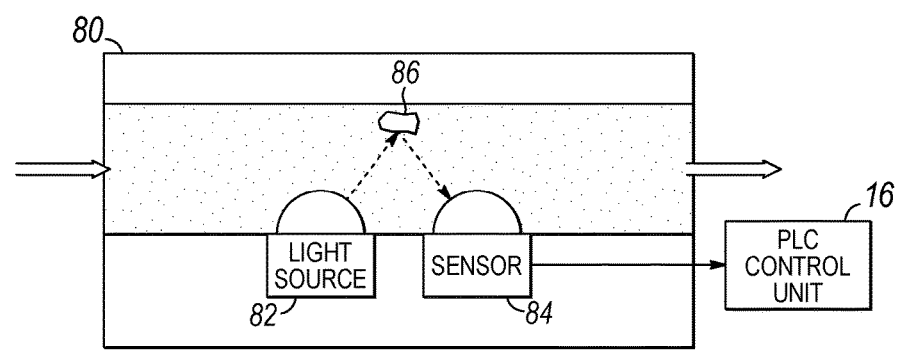
FIG. 4 is a schematic of a sensing mechanism according to an embodiment.

Referring now to FIG. 4, in an embodiment, a sensing mechanism 80 includes an emitter or light source 82 and a photo detector or sensor 84 adjacent one another. In an embodiment, the light source 82 emits infrared light. When debris passes through the optical beam, such as a particle 86, light reflects off of the particle 86 and is detected by the sensor 84. Thus, the amount of light energy that reaches the sensor 84 increases when the particle 86 passes through the optical beam. As the amount of debris in the evacuated material decreases, fewer particles are present to reflect light resulting in a signal drop.

Figure 5A:
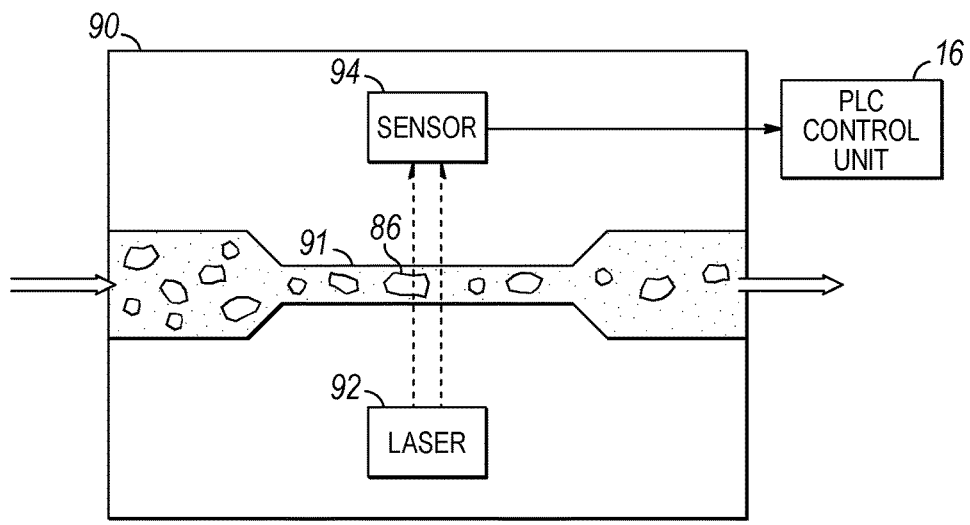
FIG. 5A is a schematic side view of another sensing mechanism according to an embodiment.
Figure 5B:
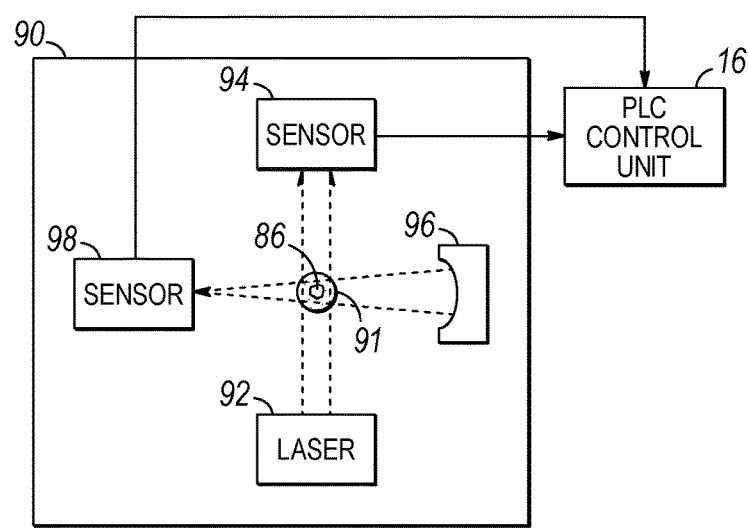
FIG. 5B is a schematic front view of the sensing mechanism of FIG. 5A.

With reference to FIGS. 5A and 5B, in another embodiment, a sensing mechanism 90 includes a laser 92, a first photo detector or sensor 94, a reflector 96, and a second photo detector or sensor 98. The evacuated material is flowing through a capillary cuvette 91. The diameter of the capillary cuvette 91 may be, for example, from about 50 micron to about 1 mm or from about 200 to about 500 micron. The laser 92 emits light that passes perpendicularly through the flowpath of the evacuated material and is detected by the first sensor 94. The amount of light energy that reaches the first sensor 94 decreases when the particle 86 passes through the optical beam. When the particle 86 passes through the light, it scatters the light. The light scatter reflects off of the reflector 96, and the reflected light is detected by the second sensor 98. The amount of light energy that reaches the second sensor 98 increases when debris passes through the optical beam. As the amount of debris in the evacuated material decreases, fewer particles are present to pass through the optical beam from the laser 92 resulting in a signal drop. Although one reflector 96 and sensor 98 pair is shown, it should be recognized that more than one sensor or sensor and reflector pair may be used to sense scattered light. The sensors may be at different angles to that shown. The evaluation by the controller 16 of the data outputs from the sensors detecting scattered light may take into account the particular configuration of the sensing mechanism (e.g., the angle of the sensor(s) to the axis of the light).

Figure 5C:
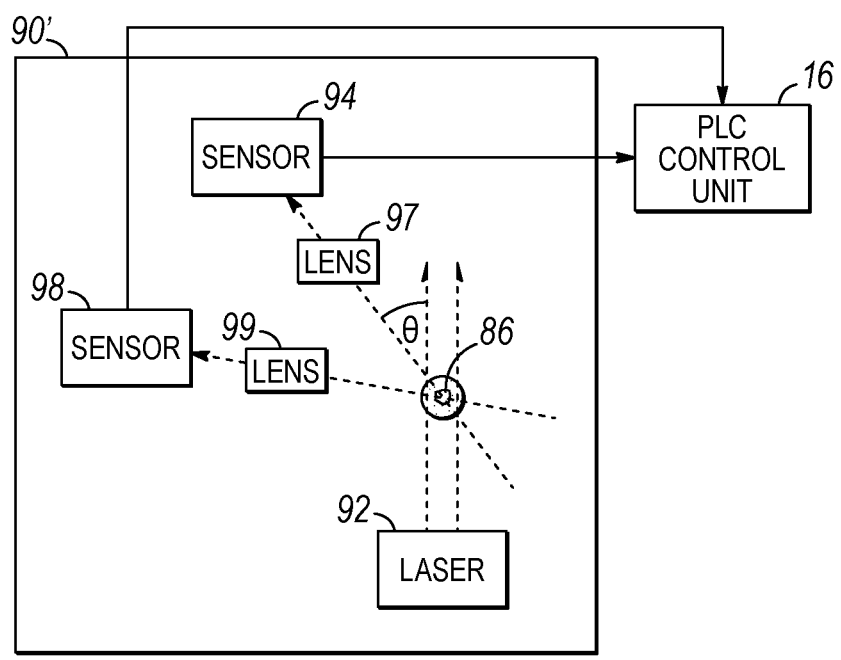
FIG. 5C is a schematic front view of another configuration of the sensing mechanism of FIG. 5A.

With reference to FIG. 5C, in another embodiment in which scattered light is sensed, a sensing mechanism 90' includes the laser 92, the first sensor 94, the second sensor 98, and lenses 97, 99. As described above, when the particle 86 passes through the light from the laser 92, it scatters the light. The light may be, for example, green light. The sensors 94, 98 are each positioned at an angle to the axis of the light from the laser 92. The lenses 97, 99 are positioned between the particle 86 and the sensors 94, 98, respectively, in the paths through which the scattered light will pass. Although two sensors 94, 98 are shown, it should be recognized that one sensor or more than two sensors may be used. The sensor(s) may be positioned at an angle in the range of 5° to 90° or 10° to 50°. For example, the angle may be 44°. As described above, the controller 16 may take into account the particular configuration of the sensing mechanism. Various features described herein may be combined. For example, the sensing mechanisms 90, 90' may include a bubble trap to eliminate the bubbles in the evacuated material to substantially stabilize the signal. The flow dynamics may be fine-tuned to avoid air bubble presence in the evacuated fluid when it passes through the sensing mechanism.

Figure 6:
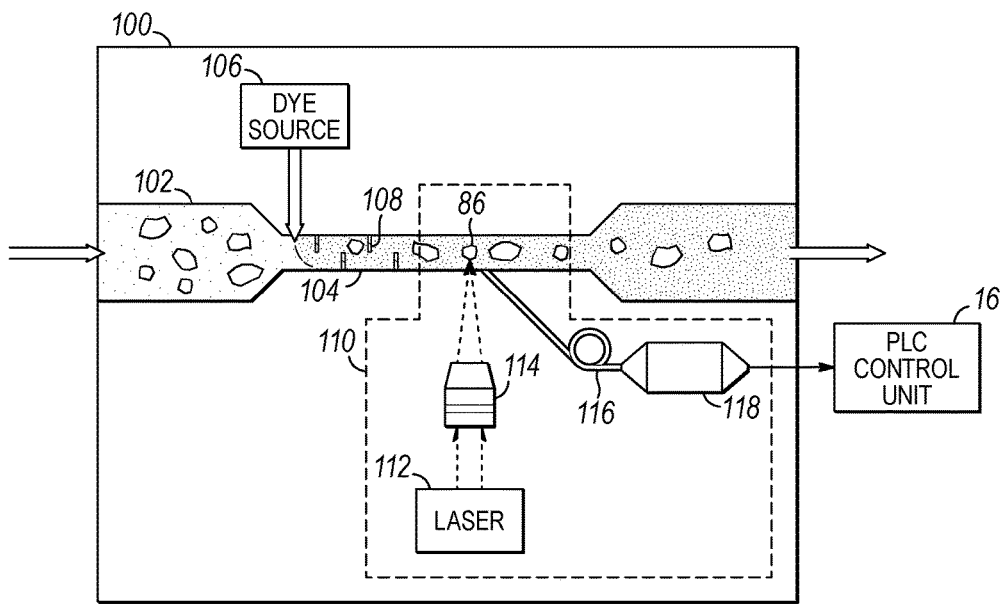
FIG. 6 is a schematic of another sensing mechanism according to an embodiment.

Referring now to FIG. 6, in another embodiment, a sensing mechanism includes a micro-optofluidic cytometer 100. The cytometer 100 includes an evacuated fluid inlet 102 and a restricted channel 104, which is smaller in cross-sectional area than the inlet 102. As the evacuated fluid enters the cytometer 100 from the inlet 102, the reduction in cross-sectional area results in a high-shear region. Additionally, the evacuated fluid inlet 102 is fluidically coupled to a dye source 106. One or more mixing elements 108 may be present to ensure the dye and evacuated fluid are sufficiently mixed so that the dye stains any debris in the evacuated fluid. The dyed fluid mixture then enters a detector 110. The detector 110 includes a laser 112, an objective lens 114, an optical fiber 116, and a multi-pixel photon counter (MPPC) photo sensor 118. The laser 112 emits light, which is focused by the lens 114 to pass through the flowpath of the fluid mixture. As the dyed particle 86 enters the optical beam, the dyed particle 86 emits fluorescent light. The emitted fluorescent light is collected via the optical fiber 116 and brought to the MPPC photo sensor 118. As the amount of debris in the evacuated material decreases, fewer particles are dyed resulting in a signal drop.

Figure 7:
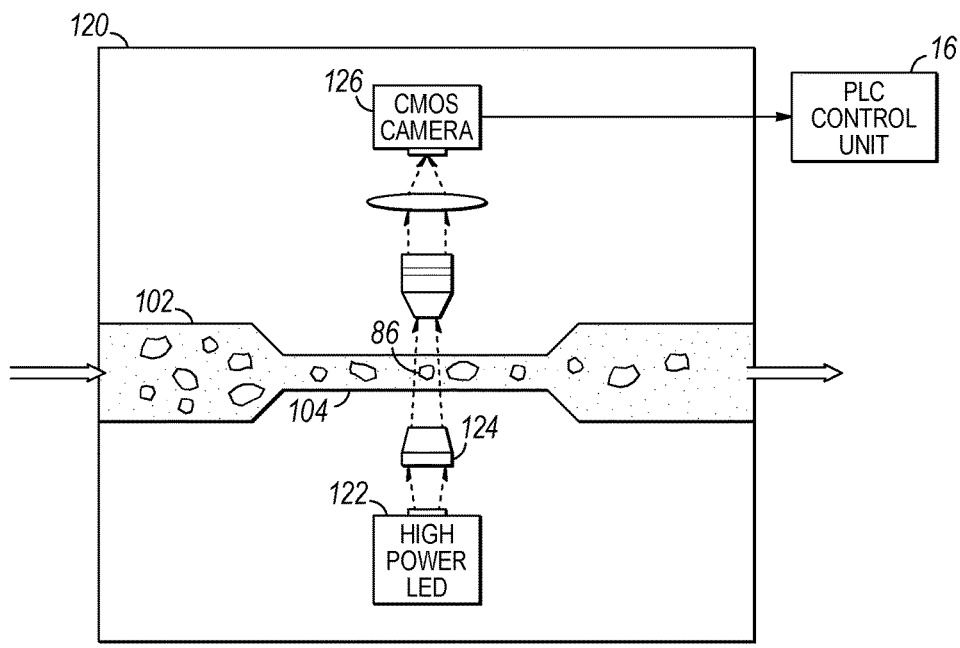
FIG. 7 is a schematic of another sensing mechanism according to an embodiment.

With reference to FIG. 7, in another embodiment, a sensing mechanism includes a real-time deformability cytometer 120. The cytometer 120 includes an LED light source 122, an objective lens 124, and a complementary metal-oxide semiconductor (CMOS) camera 126. The evacuated fluid passes through the optical beam from the LED light source 122 while in the restricted channel 104. Pictures taken from the CMOS camera 126 of the particles under shear forces show how the particles deform. The deformation determines the nature of the particles. Different types of cells deform differently under shear forces.

Figure 8:
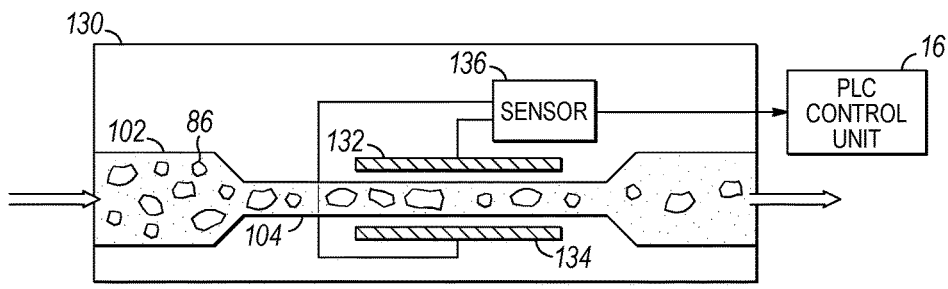
FIG. 8 is a schematic of another sensing mechanism according to an embodiment.

Referring now to FIG. 8, in another embodiment, a sensing mechanism includes an impedance sensor or an impedance spectroscopy cytometer 130. The cytometer 130 includes a first electrode 132 and a second electrode 134 each coupled to a sensor 136. The passage of a particle 86 through a field between the two electrodes 132, 134 results in a differential impedance signal. As the amount of debris in the evacuated material decreases, fewer particles pass through the field resulting in a signal drop. In an embodiment, the sensor 136 is not sensitive to air or gas bubbles and differentiates only the presence and amount of particles in the restricted channel 104. In an embodiment, the restricted channel 104 may be rectangular having inner dimensions of 1.0 mm×1.0 mm or 500 μm×500 μm or less and may provide detection of particles between 200 μm and 10 μm or less. Additionally, in an embodiment, the sensing mechanism may include a lock-in amplifier (LIA) to reduce signal noise. In another embodiment, the sensing mechanism may include impedance and dielectrophoretic force spectroscopy to sort and sense the debris particles in the evacuated fluid. In another embodiment, the sensing mechanism may sort the type of debris using single-cell impedance measurement in the restricted channel 104 by demodulating at multiple frequencies signals received from the same debris.

Figure 9:
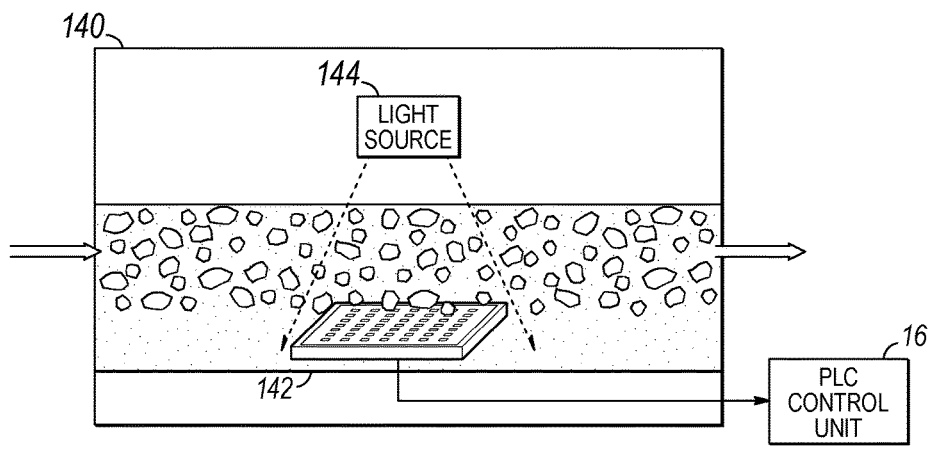
FIG. 9 is a schematic of another sensing mechanism according to an embodiment.

With reference to FIG. 9, in another embodiment, a sensing mechanism 140 includes a complementary metal-oxide semiconductor (CMOS) image biosensor array 142 and a light source 144. As the evacuated material flows through the optical beam, the CMOS image biosensor array 142 senses light input patterns of the evacuated material. As the amount of debris passing through the optical beam decreases, the amount of light energy that reaches the CMOS image biosensor array 142 increases resulting in a change in the light input patterns, which results in a signal drop. In another embodiment (not shown), a sensing mechanism may include a CMOS charge detector biosensor array, which is an array of electrodes connected to an electric circuit. The circuit may include a voltage where $V_{out}$ is equal to $V_{in}$ and has a high input impedance to prevent the input voltage signals from dropping and causing a low output impedance, which prevents signals from reducing due to loading device. There is also a constant current through the circuit from input to output. As the debris passes over the CMOS charge detector biosensor array, the debris particles interact with the CMOS charge detector biosensor array and create an electrical potential, which is sensed by the CMOS charge detector biosensor array. As the amount of debris passing over the CMOS charge detector biosensor array decreases, the electrical potential decreases, which results in a signal drop.

Figure 10:
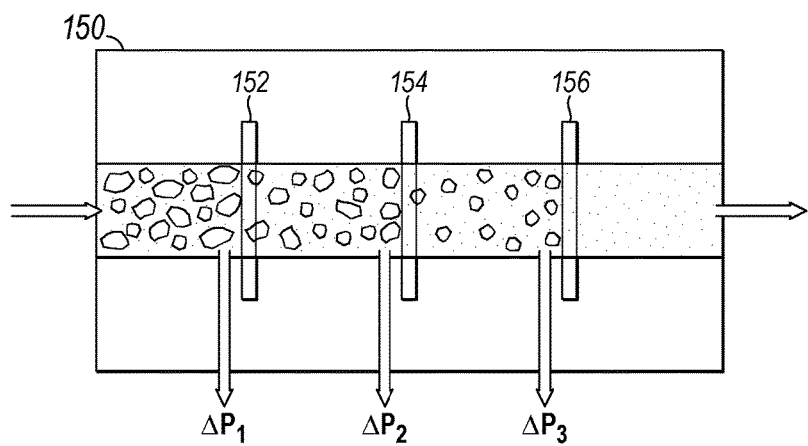
FIG. 10 is a schematic of another sensing mechanism according to an embodiment.

Referring now to FIG. 10, in another embodiment, a sensing mechanism 150 includes measuring a pressure drop to evaluate the cleanliness of the evacuated fluid. The sensing mechanism 150 includes a microfilter 152, an ultrafilter 154, and a nanofilter 156 serially positioned in the flowpath of the evacuated fluid. A pressure drop $\Delta P_1$, $\Delta P_2$, $\Delta P_3$ across each of the filters 152, 154, 156, respectively, is measured by sensors (not shown). As the evacuated material flows through the filters 152, 154, 156, the flow of any debris is restricted by the filters 152, 154, 156 depending on the size of the debris. As debris builds up on one of the filters 152, 154, 156, the pressure drop across that filter increases. As the amount of debris in the evacuated fluid decreases, the rate of change of the pressure drop decreases, which results in a signal drop. Depending on the filter sizes chosen, the presence of specific types of debris may be detected based on debris particle size. While three filters of varying sizes are illustrated, it should be recognized that the number and size of the filters may vary based on the intended application. Further, increasing the area of the filter may amplify the pressure drop signal.

Figure 11A:
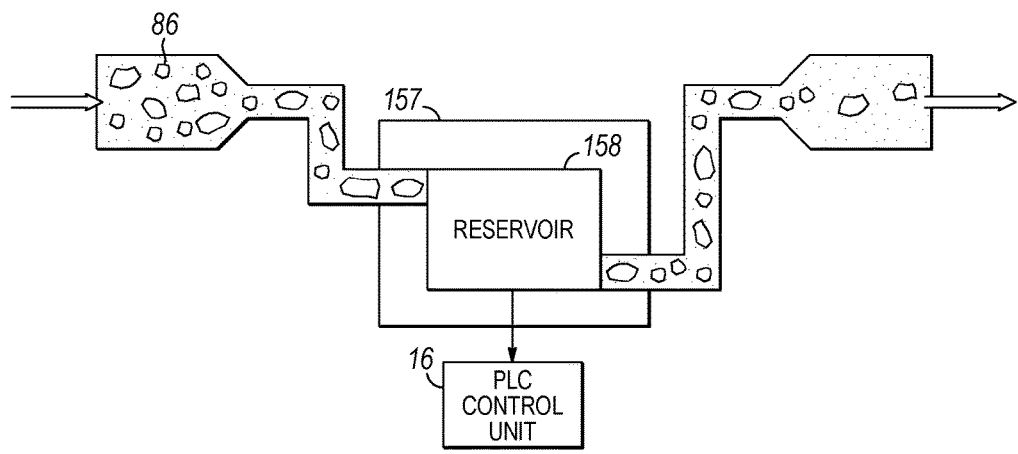
FIGS. 11A and 11B are schematics of sensing mechanisms according to various embodiments.
Figure 11B:
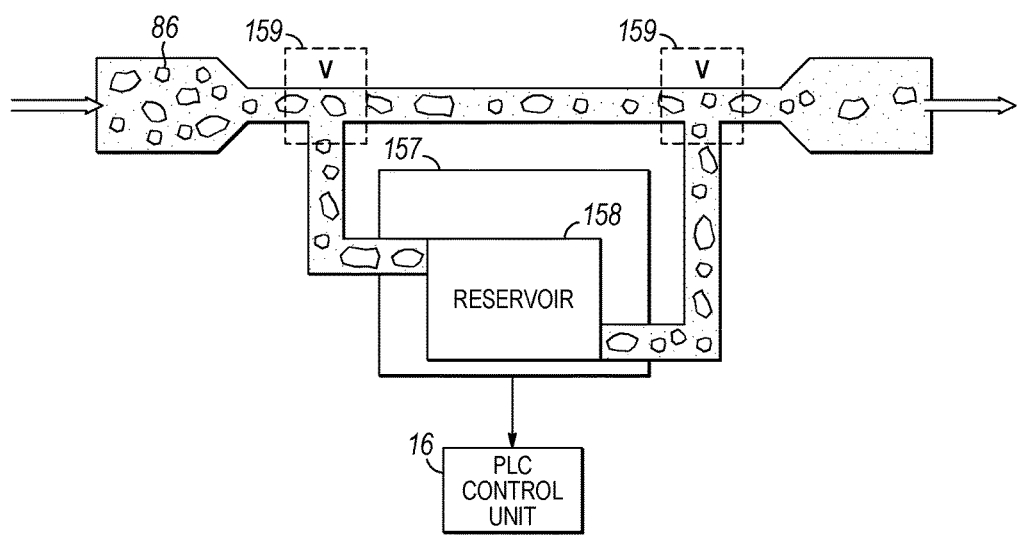

While the sensing mechanisms shown in FIGS. 1 and 4-10 are shown as being continuous flow techniques, it should be recognized that the sensing mechanism may be implemented in a semi-batch or batch configuration. With reference to FIGS. 11A and 11B, a sensing mechanism 157 is shown in a semi-batch configuration (FIG. 11A) and a batch configuration (FIG. 11B). The sensing mechanism 157 may have a variety of configurations, such any of those described with reference to FIGS. 1 and 4-10. As shown in FIG. 11A, in an embodiment, the sensing mechanism includes a reservoir 158 through which the evacuated fluid passes continuously. The reservoir 158 is sized such that the volume of evacuated fluid in the sensing mechanism 157 is increased compared to a continuous flow configuration. As shown in FIG. 11B, in an embodiment, the evacuated fluid may bypass the sensing mechanism 157 via three-way valves 159. When a reading is to be taken, the valves 159 may be adjusted so that evacuated fluid flows into the sensing mechanism 157. Both of the semi-batch and batch configurations allow for the evacuated fluid to have a longer residency time in the reservoir 158 compared to the residency time in a sensing mechanism that has a continuous configuration. A longer residence time may, for example, allow for a reaction to proceed for a desired length of time before the evacuated fluid exits the sensing mechanism 157. Additionally, the larger volume of liquid contained in the sensing mechanism 157 may allow for an increased signal to noise ratio compared to a continuous configuration, although more data points may be obtained in the same period of time in the continuous configuration. It should be recognized that a particular sensing mechanism may be implemented in one or more of a continuous, semi-batch, or batch configuration. For example, the micro-optofluidic cytometer 100, which is shown in a continuous configuration in FIG. 6, may alternately be implemented in a semi-batch or batch configuration (not shown).

Figure 12:
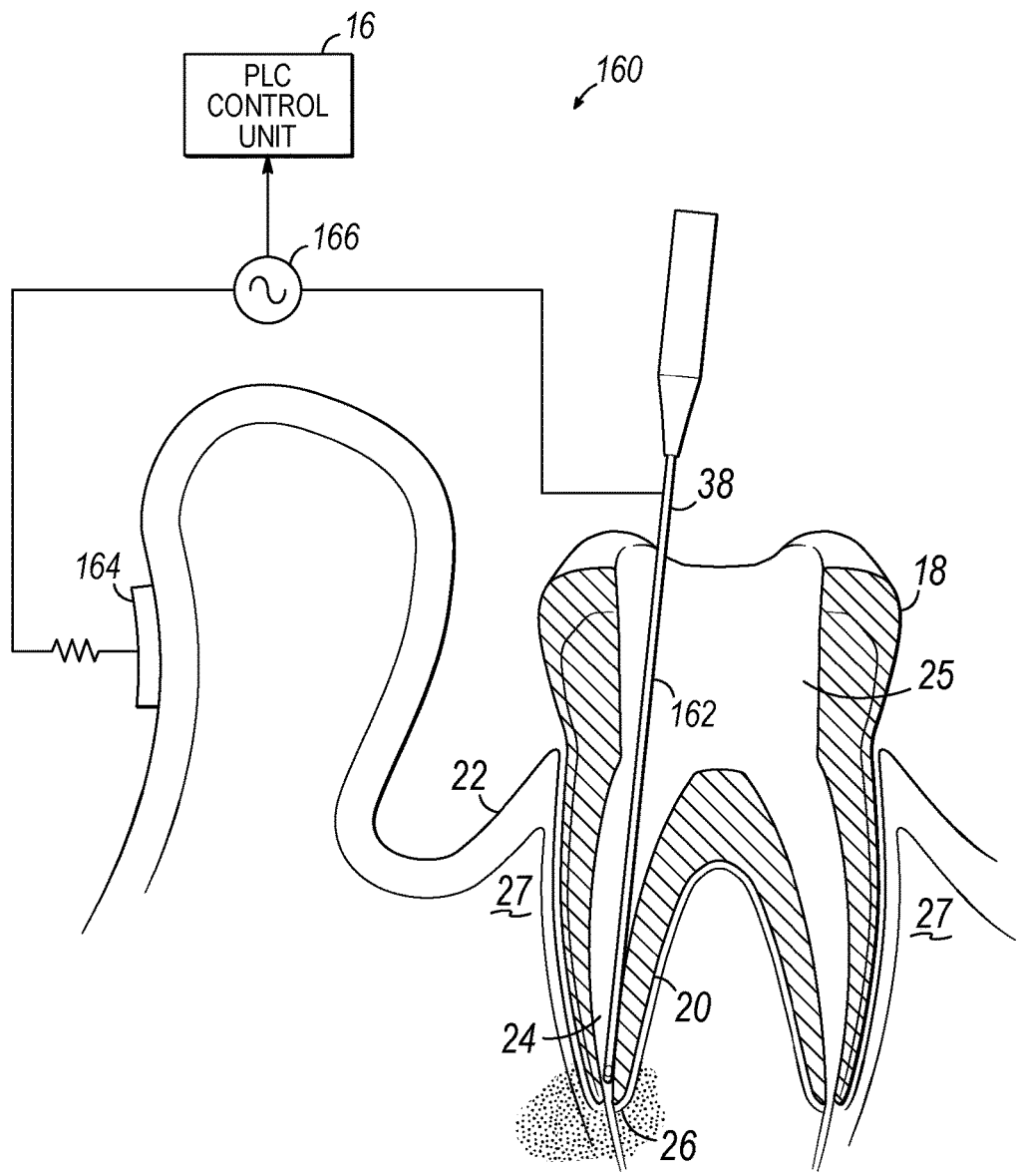
FIG. 12 is a schematic of another sensing mechanism according to an embodiment.

Referring now to FIG. 12, in another embodiment, a sensing mechanism 160 includes measuring the impedance of the fluid in the root canal 24. The sensing mechanism 160 includes a first electrode 162, a second electrode 164, and a sensor 166. In an embodiment, the microcannula 38 serves a dual-purpose and acts as the first electrode 162. The second electrode 164 may be positioned on tissue in or near the patient's mouth. In an embodiment, the second electrode 164 may be attached to the lip of the patient. The sensor 166 is capable of measuring an electric signal between the first and second electrodes 162, 164. In this configuration, the fluid is continuously flowing through the root canal 24, and any debris is being sensed while it is still in the root canal 24, which differs from the sensing mechanisms described above that sense debris in the evacuated fluid. Thus, the impedance may be measured while the root canal 24 is being cleaned. The change in impedance may indicate to the clinician whether the root canal 24 is clean or requires further flushing.

In an aspect of the present invention, a sensing mechanism may be configured to provide a distinct signal for a particular type of debris. For example, a sensing mechanism may be configured to distinguish between organic vs. inorganic debris. This may be in addition to generally sensing the presence and/or amount of debris in the evacuated irrigant. As described above, in an embodiment, a two-flush system may be used: a first flush of EDTA to remove inorganic matter, and a second flush of NaClO to remove the remaining organic matter. During the first flush, the sensing mechanism may be used to assess the presence and concentration of inorganic matter vs. organic matter. A determination by the sensing mechanism that there is no inorganic matter in the evacuated fluid indicates to the clinician that the second flush may begin. In another embodiment, a sensing mechanism may be configured to specifically sense blood There are instances where blood may overwhelm sensing data. Providing a distinct signal for the presence and/or amount of blood provides feedback for the device or the clinician to correct for the signal of the blood in the data. Additionally, the clinician may have a concern about a particular type of debris. Providing a distinct signal allows the clinician to observe whether and to what extent that debris is present throughout the procedure. This may be advantageous where, for example, the clinician is alerted if a relatively large amount of blood is in the evacuated irrigant.

In another aspect of the present invention, a sensing mechanism may include more than one sensing technique, such as those described above. For example, a device may include a spectrometer to measure absorbance and a sensor to measure the angular light scattering. The different functions of the sensing mechanism may overlap or may be different. In one aspect, one of the sensing techniques may be able to sense debris of a certain size, which is not within the operable range of the other sensing technique. For example, depending on the scattering sensor configuration, debris that is too small to be effectively measured by the scattering sensor may be sensed by the spectrometer. In another embodiment, the spectrometer may be used to determine whether blood is in the evacuated irrigant, while the scattering sensor is used to generally determine whether any debris is in the evacuated irrigant. The relative level of blood may be indicated to the clinician and, as described above, the clinician may determine whether an unusual amount of blood is present in the evacuated irrigant.

Figure 13:
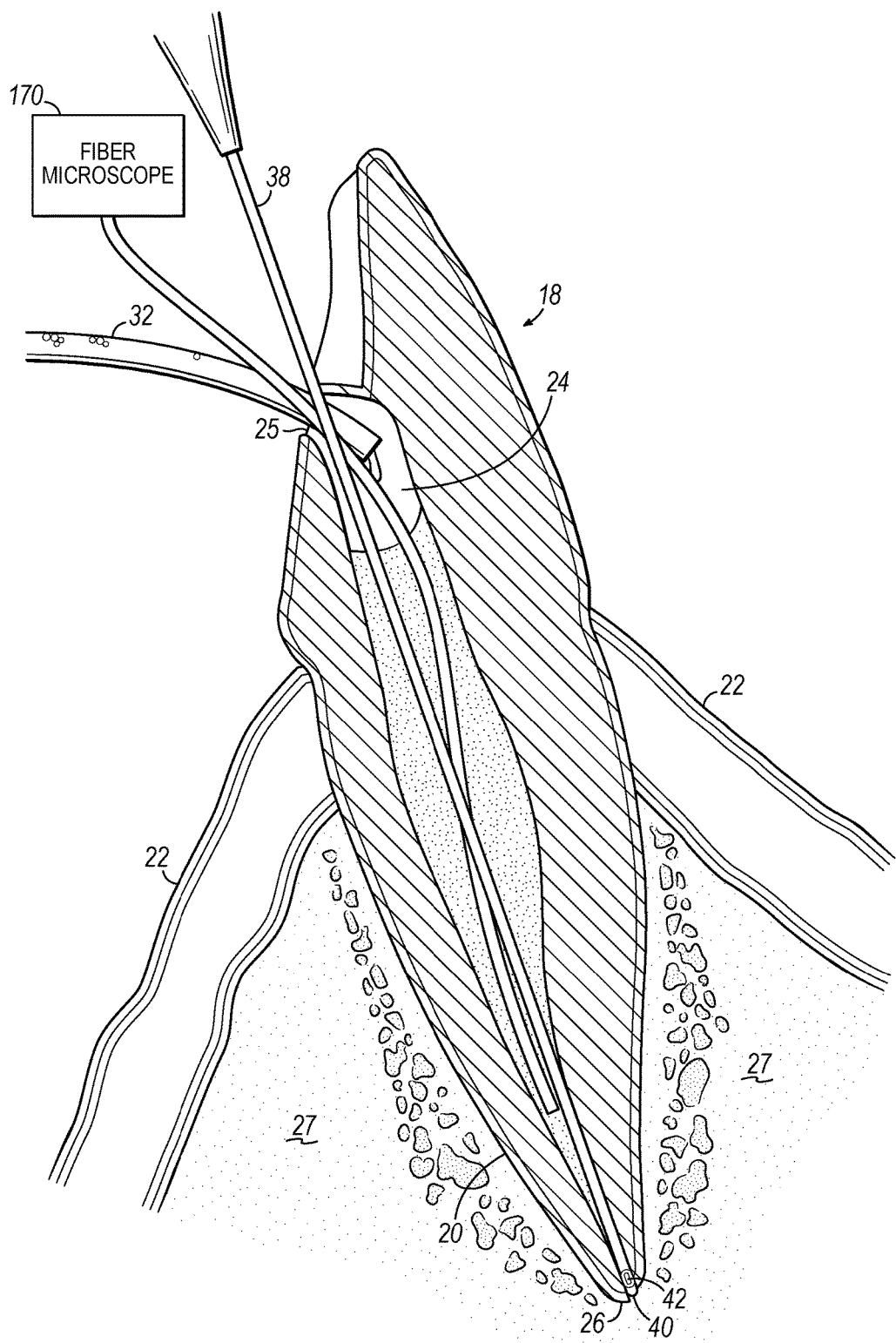
FIG. 13 is a schematic of another sensing mechanism according to an embodiment.

With reference to FIG. 13, in another embodiment, a system for determining the effectiveness of root canal debridement includes a flexible fiber microscope 170. The microscope 170 is used to visually inspect the root canal 24 during at least a portion of the root canal treatment. For example, when the microcannula 38 is inserted into the root canal 24, the microscope 170 may also be inserted. In conjunction with evaluating the cleanliness of fluid evacuated from the root canal 24 with a sensing mechanism, the clinician will be able to evaluate the visual change from a dirty root canal 24 to a clean root canal 24 using the microscope 170. Further, in an embodiment, a dye may be used to visualize specific materials, biological or other, more easily.

In an embodiment, a method for debriding may include using one irrigant to clean and etch the root canal 24. The irrigant containing, for example, an aqueous solution containing an amount of calcium di sodium EDTA ($CaNa_2EDTA$) and 2.5% stabilized sodium hypochlorite may be delivered to the root canal 24. The sodium hypochlorite acts to bleach the root canal 24, and the EDTA salt etches the root canal 24. Because the irrigant accomplishes multiple steps (i.e., bleaching and etching), the number of solutions used during the root canal procedure is reduced. Further, in an embodiment, one irrigant may be used to accomplish the cleaning, etching, and measurement of the cleanliness of the root canal 24. The irrigant may contain, for example, an aqueous solution containing an amount of $CaNa_2EDTA$, an amount of PEG-8000, and 2.5% stabilized sodium hypochlorite. In addition to the bleaching and etching effects of the sodium hypochlorite and the EDTA salt, respectively, the PEG increases the turbidity signal of the fluid. The fluid may be evacuated from the root canal 24 and evaluated by a sensing mechanism.

In order to facilitate a more complete understanding of the embodiments of the invention, the following non-limiting example is provided.

Example 1

A device was used to test sensing of shrimp (*Litopenaeus setiferus*) tissue, which is a test model for human root pulp, at different doses in a range of clinical interest. The device included a 50 mm pathlength cell, a UV/Visible light source, and a spectrophotometer detector connected with light cables. The shrimp tissue was diluted in 17% disodium EDTA. Additionally, heparinized calves blood was also diluted and sensed on the device at a higher concentration, which also is of clinical importance. The shrimp tissue and calves blood samples were prepared to represent clinical root canal treatment effluents.

The results are shown in Table 1. Table 1 shows the unprocessed signal from the detector along with the calculated transmittance and absorbance values. The signal noise was set to 100 units to determine the resolution of the readings in the range of interest.

TABLE 1

Tissue and Blood Signals vs. Wavelength in 50 mm Pathlength Flow Cell

| Sample | Dose (µg/mL) | λ (nm) | ADC Signal | Transmittance (%) | Absorbance (AU) | Resolution (µg/mL) |
|---|---|---|---|---|---|---|
| L. setiferus | 50 | 296 | 28871 | 45.1% | 0.346 | 2.90 |
| L. setiferus | 100 | 296 | 27146 | 42.4% | 0.372 | |
| L. setiferus | 50 | 320 | 29528 | 46.1% | 0.336 | 9.57 |
| L. setiferus | 100 | 320 | 27920 | 43.6% | 0.36 | |
| Calves Blood | 500 | 296 | 63926 | 99.9% | 0.001 | — |
| Calves Blood | 500 | 320 | 63925 | 99.9% | 0.001 | — |
| Calves Blood | 500 | 405 | 16794 | 26.2% | .581 | — |

The results show that the model root canal tissue, *L. setiferus*, was sensed with good resolution in a dose range of clinical interest in the range of 296 nm to 320 nm. Using the 50 mm pathlength, the absorbances are in a range of absorbance units considered excellent by chemists for analysis (e.g., 0.050 AU to 0.500 AU). The results also demonstrate that blood in moderate quantities, which sometimes is found in root canals, does not overwhelm or mask the signal in the tissue range, although it is strongly read at a wavelength typically used for blood determination (405 nm). This permits a device to read tissue values and alert the dentist to excessive blood levels simultaneously or to stop reading if a very high level of blood is detected during the procedure.

While specific embodiments have been described in considerable detail to illustrate the present invention, the description is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A method for continuously evaluating the effectiveness of debridement of a root canal of a tooth in real time, the tooth having an open access cavity and an apex end, the method comprising:
    delivering a fluid and a reagent to the open access cavity of the tooth, wherein a detectable property of the reagent changes when the reagent is mixed with an amount of debris;
    evacuating the fluid near the apex end of the tooth such that the fluid flushes most of the root canal before being evacuated; and
    continuously evaluating the evacuated fluid for at least one of a presence of debris, a concentration level of the debris, or a type of the debris, and determining a change in the detectable property of the reagent in real time.

2. The method of claim 1, further comprising:
    inserting a microcannula or a macrocannula through the open access cavity such that a tip of the microcannula or the macrocannula is positioned near the apex end of the tooth,
    wherein evacuating the fluid includes evacuating the fluid through the microcannula or the macrocannula.

3. The method of claim 1, wherein continuously evaluating the evacuated fluid includes using a sensing mechanism, and the method further comprises:
    delivering at least a portion of the evacuated fluid to the sensing mechanism.

4. The method of claim 3, wherein the sensing mechanism includes a sensor coupled to a controller, and the method further comprises:
    delivering a signal from the sensor to the controller; and
    indicating a status of the evacuated fluid based on the signal in real time.

5. The method of claim 3, wherein the sensing mechanism includes a light source, a first sensor that detects an absorbance of the debris, and a second sensor that evaluates light scattering from the debris.

6. The method of claim 1, further comprising:
    determining whether the debridement of the root canal is complete based on the evaluation of the evacuated fluid.

7. The method of claim 1, wherein delivering the fluid includes delivering a detergent.

8. The method of claim 1, wherein the reagent is a protein reagent.

9. The method of claim 1, wherein the detectable property of the reagent is a color of the reagent.

10. The method of claim 1, further comprising:
   irrigating the root canal before delivering the fluid.

11. The method of claim 1, wherein delivering the fluid includes delivering an aqueous solution comprising:
   an amount of calcium disodium ethylenediaminetetraacetic acid ($CaNa_2EDTA$);
   an amount of polyethylene glycol; and
   2.5% stabilized sodium hypochlorite.

12. The method of claim 1, wherein continuously evaluating the evacuated fluid includes determining a presence of inorganic debris, the method further comprising:
   delivering a second fluid to the open access cavity of the tooth in response to a determination that no inorganic debris is in the evacuated fluid.

13. The method of claim 12, wherein the fluid is an ethylenediaminetetraacetic acid solution and the second fluid is a sodium hypochlorite solution.

14. An apparatus for use in debriding a root canal of a tooth comprising:
   a microcannula or a macrocannula configured to evacuate a fluid in the root canal; and
   a sensing mechanism fluidically coupled to the microcannula or the macrocannula, the sensing mechanism configured to continuously sense debris in the evacuated fluid in real time, wherein the sensing mechanism includes a light source comprising a laser, a first sensor configured to detect light from the laser, a reflector, and a second sensor configured to detect light reflected off of the reflector.

15. The apparatus of claim 14, wherein the first sensor or the second sensor measures a fluorescence of the evacuated fluid.

16. The apparatus of claim 14, wherein the first sensor or the second sensor measures a turbidity of the evacuated fluid.

17. The apparatus of claim 14, wherein the first sensor and the second sensor are selected, independently, from the group consisting of: a photodiode, a multi-pixel photon counter (MPPC) photo sensor, a complementary metal-oxide semiconductor (CMOS) camera, and a CMOS image biosensor array.

18. The apparatus of claim 14, wherein the sensing mechanism includes a long pathlength capillary cuvette.

19. The apparatus of claim 14, wherein the sensing mechanism includes a CMOS charge detector biosensor array.

20. The apparatus of claim 14, wherein the sensing mechanism includes a micro-optofluidic cytometer, a real-time deformability cytometer, an impedance spectroscopy cytometer, or a single cell impedance cytometer.

21. The apparatus of claim 14, wherein the sensing mechanism includes one or more filters and a sensor for measuring a pressure drop across each of the filters.

22. The apparatus of claim 14, further comprising:
   a controller configured to receive a signal from the sensing mechanism and to continuously determine at least one of a presence of the debris, a concentration level of the debris, or a type of the debris.

23. The apparatus of claim 22, wherein the controller is configured to control the delivery of the fluid to the root canal.

24. The apparatus of claim 22, further comprising:
   an indicator coupled to the controller and configured to indicate the at least one of the presence, the concentration level, or the type of debris in real time.

25. The apparatus of claim 14, further comprising:
   a fiber microscope for viewing an interior of the root canal.

26. The apparatus of claim 14, further comprising:
   a delivery tube for delivering the fluid to the root canal.

27. The apparatus of claim 26, further comprising:
   a fluid reservoir fluidically coupled to the delivery tube.

28. The apparatus of claim 14, wherein the fluid is a detergent.

29. The apparatus of claim 14, wherein the fluid is a reagent that reacts when mixed with the debris in the root canal.

30. The apparatus of claim 14, further comprising:
   a bubble trap fluidically coupled to the microcannula or the macrocannula and the sensing mechanism.

31. The apparatus of claim 14, further comprising:
   a vacuum source.

32. An apparatus for use in debriding a root canal of a tooth comprising:
   a microcannula or macrocannula configured to evacuate a fluid in the root canal; and
   a sensing mechanism including a light source and at least one sensor, the sensing mechanism fluidically coupled to the microcannula or the macrocannula and configured to continuously sense debris in the evacuated fluid in real time, wherein the sensing mechanism includes a reflective object and the sensor detects light that reflects off of the reflective object.

33. An apparatus for use in debriding a root canal of a tooth comprising:
   a microcannula or a macrocannula configured to evacuate a fluid in the root canal; and
   a sensing mechanism including a light source, a first sensor that detects an absorbance of the debris and a second sensor that evaluates light scattering from the debris, wherein the sensing mechanism is fluidically coupled to the microcannula or the macrocannula and is configured to continuously sense debris in the evacuated fluid in real time.

34. An apparatus for use in debriding a root canal of a tooth comprising:
   a delivery tube for delivering fluid to the root canal; and
   a sensing mechanism configured to continuously sense debris in the fluid comprising:
     a first electrode;
     a second electrode comprising a microcannula or a macrocannula configured to evacuate the fluid in the root canal; and
     a sensor coupled to the first and second electrodes.

35. A method for debriding a root canal of a tooth, the tooth having an open access cavity and an apex end, the method comprising:
   delivering a fluid to the open access cavity of the tooth, the fluid including an aqueous solution comprising:
     an amount of calcium disodium ethylenediaminetetraacetic acid ($CaNa_2EDTA$); and
     2.5% stabilized sodium hypochlorite.

36. The method of claim 35, further comprising:
   evacuating the fluid near the apex end of the tooth such that the fluid flushes the root canal before being evacuated.

37. The method of claim 36, further comprising:
   continuously evaluating the evacuated fluid for at least one of a presence of debris, a concentration level of the debris, or a type of the debris.

* * * * *